(12) United States Patent
Colli et al.

(10) Patent No.: US 7,939,676 B2
(45) Date of Patent: May 10, 2011

(54) PROCESS FOR THE PREPARATION OF LEVETIRACETAM

(75) Inventors: Corrado Colli, Galliate (IT); Massimiliano Forcato, Galzignano Terme (IT); Livius Cotarca, Cervignano Del Friuli (IT)

(73) Assignee: Zach System S.p.A., Bresso (MI) (IT)

( * ) Notice: Subject to any disclaimer, the term of this patent is extended or adjusted under 35 U.S.C. 154(b) by 0 days.

(21) Appl. No.: 12/561,616

(22) Filed: Sep. 17, 2009

(65) Prior Publication Data

US 2011/0065932 A1    Mar. 17, 2011

(51) Int. Cl.
*C07D 207/06* (2006.01)
*C07D 207/08* (2006.01)

(52) U.S. Cl. .................................. 548/552; 548/551

(58) Field of Classification Search ............ 548/551, 548/552
See application file for complete search history.

(56) References Cited

U.S. PATENT DOCUMENTS

| 4,837,223 | A | 6/1989 | Gobert et al. |
| 6,107,492 | A | 8/2000 | Futagawa et al. |
| 6,124,473 | A | 9/2000 | Cavoy et al. |
| 7,531,673 | B2 * | 5/2009 | Acharyulu et al. ........... 548/543 |
| 2005/0182262 | A1 * | 8/2005 | Acharyulu et al. ........... 548/534 |

FOREIGN PATENT DOCUMENTS

| EP | 1566376 | 8/2005 |
| GB | 1309692 | 3/1973 |
| GB | 2225322 | 5/1990 |
| WO | 01/64637 | 9/2001 |
| WO | 03/014080 | 2/2003 |
| WO | 2004/069796 | 8/2004 |
| WO | WO 2006095362 A1 * | 9/2006 |
| WO | 2008/012268 | 1/2008 |

* cited by examiner

*Primary Examiner* — Kamal A Saeed
*Assistant Examiner* — Nyeemah Grazier
(74) *Attorney, Agent, or Firm* — Lucas & Mercanti, LLP

(57) ABSTRACT

A process for the manufacturing of levetiracetam, wherein said process comprises the steps of: (1) reacting the (−)-(S)-alpha-ethyl-2-oxo-1-pyrrolidine acetic acid with a substoichiometric amount of an activating agent in an alcoholic solvent, and (2) subjecting the resulting reaction solution of step (1) to an ammonolysis process with gaseous ammonia.

14 Claims, No Drawings

PROCESS FOR THE PREPARATION OF LEVETIRACETAM

FIELD OF THE INVENTION

The present invention relates to a process for the preparation of levetiracetam and, more particularly, to an improved process for the preparation of levetiracetam.

More in particular, the present invention relates to an improved process for the conversion of the (−)-(S)-alpha-ethyl-2-oxo-1-pyrrolidineacetic acid to levetiracetam through the activation of the carboxylic acid group and its conversion with gaseous ammonia.

BACKGROUND OF THE INVENTION

Levetiracetam, (−)-(S)-alpha-ethyl-2-oxo-1-pyrrolidineacetamide, is a drug useful as a protective agent for treating and preventing hypoxic and ischemic type aggressions of the central nervous system. It is the active ingredient of KEPPRA®, tablets and flavored liquid, indicated as adjunctive therapy in the treatment of partial onset seizures in adults and children four years of age and older with epilepsy.

Levetiracetam was first described in U.S. Pat. No. 4,837,223 (UCB Societe Anonyme) where it is stated that it has particular therapeutic properties compared to the known racemic form (non proprietary name etiracetam). The S-enantiomer, for example, has a ten times higher protective activity against hypoxia and a four times higher protective activity against cerebral ischemia than the racemic mixture.

The U.S. Pat. No. 4,837,223 describes a method for the preparation of levetiracetam which comprises reacting (−)-(S)-alpha-ethyl-2-oxo-1-pyrrolidineacetic acid successively with alkylhaloformate and with ammonia. Said acid intermediate is, in turn, obtained from racemic (±)-alpha-ethyl-2-oxo-1-pyrrolidine acetic acid by a classic optical resolution according to known methods. In example 1, ethyl (±)-alpha-ethyl-2-oxo-1-pyrrolidine acetate is hydrolyzed to give the corresponding racemic acid in the presence of sodium hydroxide; said acid is subjected to chemical resolution by reaction with an optically active base, (+)-(R)-(1-phenyl ethyl)-amine, selective crystallization of diastereoisomeric salts thereof and isolation of the desired enantiomeric form; finally, the resultant (−)-(S)-alpha-ethyl-2-oxo-1-pyrrolidineacetic acid is converted into the corresponding amide via activation of the carboxyl residue with ethyl chloroformate.

Several alternative processes for the preparation of levetiracetam have been disclosed in the art.

GB 1,309,692 (UCB S.A.) describes the preparation of several N-substituted lactams, including, inter alia, 2-(2-oxopyrrolidino)-butyramide, i.e. the racemic form of levetiracetam, by converting the corresponding ester, obtained by reacting the appropriate pyrrolidin-2-one with an appropriate alkyl haloalkylcarboxylate, with gaseous ammonia in methanol (example 2) or by converting the corresponding acid chloride, obtained by reacting the corresponding acid with thionyl chloride, with gaseous ammonia (example 3).

WO 01/64637 (UCB Farchim) describes the preparation of levetiracetam by asymmetric hydrogenation in the presence of a chiral catalyst of (Z) or (E)-2-(2-oxotetrahydro-1H-1-pyrrolyl)-2-butenamide, which in turn is obtained by reacting the corresponding acid with $PCl_5$ to give the corresponding acid chloride, and then with gaseous ammonia.

WO 03/014080 (UCB S.A.) describes a process for the preparation of levetiracetam and analogues thereof comprising the synthesis of the corresponding ester derivative, methyl-(S)-alpha-ethyl-2-oxo-1-pyrrolidine-acetate, and the subsequent ammonolysis reaction in the presence of water.

EP 1,566,376 (REDDYS LAB LTD DR) discloses a process for the preparation of levetiracetam by reacting 4-chlorobutyl chloride with (S)-2-Aminobutyramide hydrochloride, this latter being obtained by first reacting (S)-2-aminobutyric acid hydrochloride with thionyl chloride in methanol to give the corresponding ester hydrochloride, and then reacting the corresponding ester with ammonia in isopropanol.

Several other patents and patent applications describe other approaches to the synthesis of levetiracetam, such as, for example, U.S. Pat. Nos. 6,107,492 and 6,124,473 which describe the preparation of levetiracetam by optical resolution of etiracetam by means of preparative high performance liquid chromatography or continuous simulated moving bed chromatographic system, GB 2,225,322, which describes a process for the preparation of levetiracetam by hydrogenolysis of (S)-alpha-[2-(methylthio)-ethyl]-(2-oxo-1-pyrrolidine)-acetamide in the presence of a desulfurizing agent, and WO 2004/069796, which describes a process for preparing levetiracetam which comprises reacting (S)-2-aminobutyramide hydrochloride and 4-chlorobutyl chloride in a solvent selected from acetonitrile and methyl tertbutyl ether in the presence of a strong base and recovering the crude product.

Accordingly, notwithstanding the levetiracetam is known since a long time, the efforts of the industry research are still dedicated to find an process for the manufacturing thereof, and there is still the need of an optimized process.

SUMMARY OF THE INVENTION

The Applicant has faced the problem of improving the process for the preparation of levetiracetam.

More in particular, the Applicant has faced the problem of setting up a synthesis process which allows to obtain pure levetiracetam with less expensive operating conditions, improved processability, less formation of side products and consequently higher yield, and lower safety concerns.

Still more particularly, the Applicant has faced the problem of improving the conversion process of the (−)-(S)-alpha-ethyl-2-oxo-1-pyrrolidineacetic acid to levetiracetam through the activation of the carboxylic acid group and its conversion with ammonia.

After a long and difficult set of tests and experimentations, the Applicant has found that the processes known in the art for the preparation of levetiracetam have several disadvantages.

First, all the processes known in the art require the isolation of the intermediate products before the treatment with ammonia.

From an industrial point of view, this passage requires an expensive distillation and separation process to reduce to dryness the intermediate products, which reduces the yield of the whole process.

Further, the thermal treatment required for distillation often promotes the partial decomposition of the intermediate itself, with a further reduction of the yield and an increase of impurities.

Additionally, the use of stoichiometric or higher amounts of activating agents like $PCl_5$ and thionyl chloride increases the safety concerns of an industrial process using such compounds.

Finally, the formation of salts deriving from the use of such activating agents into the reaction mixture can reduce the yield of the final product and compromise the quality of crude levetiracetam. The higher the amount of activating agents, the higher the formation of such salts.

The Applicant has found that the above mentioned problems may be overcome by directly converting the (−)-(S)-alpha-ethyl-2-oxo-1-pyrrolidine acetic acid into the (−)-(S)-alpha-ethyl-2-oxo-1-pyrrolidineacetamide in the presence of a substoichiometric amount of a proper activating agent without the isolation and separation of any intermediate product.

The Applicant has surprisingly found that the use of a substoichiometric amount of a proper activating agent allows to conduct a one-pot conversion without the need of isolating the intermediate product.

The Applicant has unexpectedly found that the use of a substoichiometric amount of a proper activating agent allows to improve the quality of the crude product, so requiring a lower number of recrystallization steps in order to obtain a satisfactorily pure levetiracetam.

The Applicant has surprisingly found that the reduction to dryness of the intermediate product coming from the reaction of (−)-(S)-alpha-ethyl-2-oxo-1-pyrrolidine acetic acid with the proper activating agent promotes the decomposition to the starting product (−)-(S)-alpha-ethyl-2-oxo-1-pyrrolidine acetic acid, with a reduction of the yield, and an increase of impurities.

The Applicant has also surprisingly found that conducting and completing the conversion reaction in the same reaction solution without reducing to dryness the intermediate product allows to obtain a higher yield of crude (−)-(S)-alpha-ethyl-2-oxo-1-pyrrolidineacetamide, with a lower amount of chemical impurities derived from decomposition of the intermediate product and/or a lower amount of optical impurities derived from the formation of the (+)-(R)-enantiomer.

Accordingly, the present invention relates to a process for the manufacturing of levetiracetam, wherein said process comprises the steps of:

(1) reacting the (−)-(S)-alpha-ethyl-2-oxo-1-pyrrolidine acetic acid with a substoichiometric amount of an activating agent in an alcoholic solvent, and (2) subjecting the resulting reaction solution of step (1) to an ammonolysis process with gaseous ammonia.

Preferably, the activating agent can be thionyl chloride, phosphorus trichloride, phosphorus pentachloride, or phosgene. According to a preferred embodiment the activating agent is thionyl chloride.

Advantageously, the alcoholic solvent can be a lower alkyl alcohol, having from 1 to 6 carbon atoms, such as, for example, methanol, ethanol, propanol, isopropanol, butanol and tert-butanol. According to a preferred embodiment the alcoholic solvent is methanol.

Step (1) of the process of the present invention is preferably conducted at a temperature of from 10° to 80° C., more preferably from 20° to 70° C., and most preferably from 30° to 60° C. Advantageously, the reaction temperature is ranging from 45° to 55° C.

The activating agent is preferably added to a previously prepared solution of (−)-(S)-alpha-ethyl-2-oxo-1-pyrrolidine acetic acid in alcohol, preferably in methanol.

The amount of activating agent is substoichiometric with respect to the amount of (−)-(S)-alpha-ethyl-2-oxo-1-pyrrolidine acetic acid. The activating agent is preferably added in an amount lower than 1.00, more preferably lower than 0.90, and most preferably lower than 0.80 molar equivalent with respect the molar equivalent of (−)-(S)-alpha-ethyl-2-oxo-1-pyrrolidine acetic acid. On the other hand, the activating agent is preferably added in an amount higher than 0.20, more preferably higher than 0.30, and most preferably higher than 0.40 molar equivalent with respect the molar equivalent of (−)-(S)-alpha-ethyl-2-oxo-1-pyrrolidine acetic acid.

The Applicant has found that the use of a substoichiometric amount of activating agent, besides not substantially affecting the completion of the reaction, allows to reduce the formation of salts during the addition of ammonia, and, consequently, to improve the yield and the quality of the final product.

After completion of step (1), the reaction mixture is preferably subjected to a distillation step, wherein the volume of the reaction mixture is reduced up to 70% v/v, more preferably up to 80% v/v, and most preferably up to 90% v/v, of the original volume by distillation at moderate temperature and reduced pressure. Preferably, the distillation is conducted at a temperature of from 15° to 45° C., more preferably from 25° to 40° C., under reduced pressure. At the end of distillation, the reaction mixture can be optionally added with fresh methanol up to the initial volume.

The Applicant has found that the partial reduction of the reaction mixture volume by moderate distillation allows to substantially eliminate or reduce all the volatile compounds formed during step (1), so reducing the acidity of the reaction mixture, without promoting any decomposition of the intermediate products to the starting compound (−)-(S)-alpha-ethyl-2-oxo-1-pyrrolidine acetic acid, or racemization or conversion to the (+)-(R)-enantiomer thereof.

The Applicant has found that the reduction of the volatile compounds allows to reduce the formation of salts by addition of ammonia during the subsequent step (2). A lower formation of salts resulted in a higher quality of the resulting crude levetiracetam at the end of the step (2) with a higher yield.

After completion of step (1), the reaction mixture is preferably subjected to a neutralization step, wherein the reaction mixture is treated with a base, more preferably with gaseous ammonia up to a pH ranging from 4.0 to 10.0, preferably from 5.0 to 9.0.

The correction of pH promotes the formation of salts which can be easily separated from the reaction mixture by filtration. The pH correction and the separation of the formed salts further allows to reduce the formation of salts by addition of ammonia during the subsequent step (2), and, as already mentioned above, resulted in a higher quality of the resulting crude levetiracetam at the end of the step (2) with a higher yield.

After completion of step (1), optionally including the distillation step and the neutralization step described above, the reaction mixture is directly subjected to step (2) of the present invention.

In a preferred embodiment of the present invention, the ammonolysis process of step (2) is conducted under pressure, preferably under a pressure of from 0.5 bar to 5 bar, more preferably from 1.5 bar to 3.5 bar, over the standard atmospheric pressure. Most preferably, the ammonolysis process of step (2) is conducted at a pressure of about 3 bar over the standard atmospheric pressure.

Preferably, the ammonolysis process is conducted in anhydrous condition using gaseous ammonia bubbled into the methanolic reaction mixture in a reactor pressurized with ammonia gas up to the desired pressure. The absence of water allows to avoid decomposition of the intermediate products to the starting compound (−)-(S)-alpha-ethyl-2-oxo-1-pyrrolidine acetic acid, or racemization or conversion to the (+)-(R)-enantiomer thereof.

During the ammonolysis process, the temperature is maintained in the range of from 0° C. to 40° C., preferably from 10° C. to 30° C., and more preferably from 15° C. to 25° C. Most preferably, the ammonolysis process is conducted at about 20° C.

After completion of the conversion to levetiracetam, the crude levetiracetam is collected by means of conventional crystallization procedures.

Preferably, the methanolic reaction mixture coming from the ammonolysis process is distilled at moderate temperature and reduced pressure until to be reduced to the minimum volume, typically ranging from 5 to 20% v/v with respect the initial volume. Preferably, the methanolic reaction mixture is distilled at a temperature of from 30° to 45° C., more preferably from 35° to 40° C., under reduced pressure.

The crude levetiracetam is recovered by recrystallization from conventional solvents employed in the art for the crystallization of levetiracetam, such as, for example, ketones, like acetone and MEK, hydrocarbons, or halogenated hydrocarbon, like dichloromethane, and the like. Preferably, the recrystallization solvent employed in the process of the present invention is acetone. The recrystallization solvent is added to the residual mixture, the solution is refluxed for a period of time ranging from 10 minutes to 5 hours, preferably from 15 minutes to 1 hour, and then slowly cooled up to precipitation of levetiracetam, which is separated by filtration.

The crude levetiracetam obtained with the process of the present invention shows a grade of purity higher than 90% w/w, preferably higher than 95% w/w, with a content of (R)-enantiomer lower than 5.0% w/w, preferably lower than 2% w/w.

The high grade of chemical and optical purity of the crude levetiracetam obtained with the process of the present invention allows to obtain the levetiracetam end product with the desired grade of chemical and optical purity with only one further single purification step.

This is a further advantage of the process of the present invention. In fact, the reduction of the number of purification steps means a simpler and less expensive process, due to the reduction of time and occupation of the plant, and a higher yield, due to the reduction of product loss.

The purification step is conducted with the same crystallization solvents described above. Preferably, the recrystallization solvent employed in the purification step is acetone.

The pure levetiracetam obtained after the purification step shows a grade of purity higher than 96% w/w, preferably higher than 98% w/w, with a content of (R)-enantiomer lower than 1.0% w/w, preferably lower than 0.1% w/w.

From the detailed description above, it is therefore readily apparent that the process of the present invention shows several advantages with respect to the processes already described in the art.

For better illustrating the invention the following non-limiting examples are now given.

EXAMPLE 1

Invention

Step 1

(−)-(S)-alpha-ethyl-2-oxo-1-pyrrolidine acetic acid (150 g, 0.87 mol) was dissolved in methanol (235 g, 300 ml) at 45° C. and thionyl chloride (56 g, 0.47 mol) was added dropwise over 30 min.

The reaction mixture was stirred at 45° C. for additional 15-30 min until complete conversion of (−)-(S)-alpha-ethyl-2-oxo-1-pyrrolidine acetic acid was observed via HPLC (unreacted (−)-(S)-alpha-ethyl-2-oxo-1-pyrrolidine acetic acid ≦2%, by HPLC % area).

At reaction completed, the volatiles were distilled off at moderate temperature and reduced pressure (35°-40° C., 150-200 mbar) until 10% of the whole volume was eliminated, then the mixture was reintegrated with fresh methanol up to initial volume.

After that, the reaction mixture was neutralized by bubbling ammonia gas at 20° C. up to a pH value equal to about 5, and stirred at 20° C. for 1 h. A limited amount of salts (about 44 g) precipitated and was filtered off. The resulting methanol solution was directly transferred to the autoclave.

Step 2

The reaction mixture was pressurized up to about 3 bar with ammonia gas at 20° C., and stirred until complete conversion to (−)-(S)-alpha-ethyl-2-oxo-1-pyrrolidineacetamide was observed via HPLC.

Then, once the reaction mixture was taken out of the autoclave, the residual salts formed (about 20 grams) were filtered off and the methanol solution was distilled up to a minimum volume at moderate temperature and reduced pressure (35°-40° C., 150-200 mbar).

Acetone (115 ml) was added and the mixture was distilled again at moderate temperature and reduced pressure (35°-40° C., 150-200 mbar) to minimum volume. After that acetone (300 ml) was charged over the residue and the mixture was heated and refluxed for 30 minutes. Finally, the solution was cooled down slowly to 0° C. and crude levetiracetam was isolated by filtration.

Crude levetiracetam (molar yield 73.1%, (R)-enantiomer: 1.171%) was then submitted to a final purification process in one step to give pure levetiracetam.

Acetone (750 ml) was charged over crude levetiracetam and the mixture was again stirred and heated to reflux. Once refluxed for about 30 minutes the hot mixture was filtered to remove residual salts and cooled slowly to 0° C.

Pure levetiracetam ((R)-enantiomer: 0.01%) was obtained by filtration and drying under vacuum at 40° C. Overall molar yield was 60.0% by mole of the starting amount of (−)-(S)-alpha-ethyl-2-oxo-1-pyrrolidine acetic acid (ponderal yield 78.4% by weight).

EXAMPLE 2

Example 1 was repeated, but the neutralization step with ammonia at the end of step 1 was omitted. At the end of step 2, crude levetiracetam was isolated (molar yield 73.1%, (R)-enantiomer: 2.21%). After purification step, pure levetiracetam (molar yield 64.4%, (R)-enantiomer: 0.58%) was obtained.

EXAMPLE 3

Comparison

Step 1 of Example 1 was repeated using an excess of thionyl chloride (114 g, 0.96 mol) with respect to (−)-(S)-alpha-ethyl-2-oxo-1-pyrrolidine acetic acid. Further, when the complete conversion of (−)-(S)-alpha-ethyl-2-oxo-1-pyrrolidine acetic acid was observed, the reaction mixture was distilled off at moderate temperature and reduced pressure (35°-40° C., 150-200 mbar) until dryness. Decomposition of about 13% by weight of the intermediate product to starting product (−)-(S)-alpha-ethyl-2-oxo-1-pyrrolidine acetic acid was observed.

EXAMPLE 4

Effect of Activating Agent Amount

Example 1 was repeated using different amount of thionyl chloride as reported in the following Table 1. The amount of thionyl chloride is expressed in terms of equivalent with respect to (−)-(S)-alpha-ethyl-2-oxo-1-pyrrolidine acetic acid.

TABLE 1

| Sample | SOCl$_2$ | Conversion Time (hours) | Unreacted (% w/w) | Converted (% w/w) |
|---|---|---|---|---|
| 1 | 1.10 | 1 | 0.1 | 99.9 |
| 2 | 0.78 | 0.5 | 0.4 | 99.7 |
| 3 | 0.60 | 1 | 1.1 | 99.3 |
| 4 | 0.54 | 0.5 | 1.1 | 99.3 |
| 5 | 0.29 | 2 | 2.2 | 98.4 |
| 6 | 0.09 | 5 | 4.9 | 96.7 |
| 7 | 0.05 | 24 | 1.7 | 99.0 |

The data of Table 1 clearly show that the use of a substoichiometric amount of thionyl chloride (samples 2 to 5) does not substantially affect the conversion time and conversion yield of (−)-(S)-alpha-ethyl-2-oxo-1-pyrrolidine acetic acid. On the contrary, the use of catalytic amount of thionyl chloride (samples 6 and 7) substantially increases the conversion time and/or the conversion yield.

The use of equivalent or even higher amount of thionyl chloride is not desirable from several point of view.

The Applicant has found that the higher the amount of thionyl chloride, the higher is the residual acidity of the resulting reaction solution, the higher is the amount of salt formation during ammonolysis. As these salts tend to precipitate together with levetiracetam, they would seriously compromise the quality of the crude product, so requiring several recrystallization steps in order to obtain a satisfactorily pure levetiracetam.

The invention claimed is:

1. A process for the manufacturing of levetiracetam, wherein said process comprises the steps of:
   (1) reacting the (−)-(S)-alpha-ethyl-2-oxo-1-pyrrolidine acetic acid with a substoichiometric amount of an activating agent in an alcoholic solvent, and
   (2) subjecting the resulting reaction solution of step (1) to an ammonolysis process with gaseous ammonia,
   wherein said activating agent is selected from the group consisting of thionyl chloride, phosphorus trichloride, phosphorus pentachloride and phosgene.

2. The process according to claim 1, wherein said activating agent is thionyl chloride.

3. The process according to claim 1, wherein said alcoholic solvent is selected from the group consisting of methanol, ethanol, propanol, isopropanol, butanol and tert-butanol.

4. The process according to claim 3, wherein said alcoholic solvent is methanol.

5. The process according to claim 1, wherein said activating agent is added in an amount lower than 0.90 and higher than 0.30 molar equivalent with respect the molar equivalent of (−)-(S)-alpha-ethyl-2-oxo-1-pyrrolidine acetic acid.

6. The process according to claim 5, wherein said activating agent is added in an amount lower than 0.80 and higher than 0.40 molar equivalent with respect the molar equivalent of (−)-(S)-alpha-ethyl-2-oxo-1-pyrrolidine acetic acid.

7. The process according to claim 1, wherein the reaction mixture of said step (1) is subjected to a neutralization step raising the pH of said reaction mixture within a range of from 4.0 to 10.0.

8. The process according to claim 7, wherein the reaction mixture of said step (1) is subjected to a neutralization step raising the pH of said reaction mixture within a range of from 5.0 to 9.0.

9. The process according to claim 7, wherein said neutralization step is made with gaseous ammonia.

10. The process according to claim 1 wherein said ammonolysis process is conducted under pressure.

11. The process according to claim 10, wherein said ammonolysis process is conducted under a pressure of from 0.5 bar to 5 bar over the standard atmospheric pressure.

12. The process according to claim 10, wherein said ammonolysis process is conducted in anhydrous condition with ammonia gas.

13. The process according to claim 1, where the crude levetiracetam is recovered from said reaction mixture by recrystallization from acetone.

14. The process according to claim 13, wherein the crude levetiracetam obtained with said process shows a grade of chemical purity higher than 95% w/w, with a content of (R)-enantiomer lower than 2% w/w.

* * * * *